United States Patent
Arakawa et al.

(10) Patent No.: US 8,246,961 B2
(45) Date of Patent: Aug. 21, 2012

(54) POWDER COMPOSITION, METHOD FOR PRODUCING THE SAME, AND FOOD COMPOSITION, COSMETIC COMPOSITION AND PHARMACEUTICAL COMPOSITION CONTAINING THE SAME

(75) Inventors: Jun Arakawa, Kanagawa (JP); Shinichiro Serizawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 346 days.

(21) Appl. No.: 12/440,667

(22) PCT Filed: Feb. 5, 2008

(86) PCT No.: PCT/JP2008/052215
§ 371 (c)(1),
(2), (4) Date: Mar. 10, 2009

(87) PCT Pub. No.: WO2008/096888
PCT Pub. Date: Aug. 14, 2008

(65) Prior Publication Data
US 2010/0055191 A1    Mar. 4, 2010

(30) Foreign Application Priority Data

Feb. 6, 2007  (JP) ................. 2007-027287
Jul. 2, 2007   (JP) ................. 2007-174556

(51) Int. Cl.
*A61K 36/02* (2006.01)
*A61K 47/00* (2006.01)
*A23L 1/00* (2006.01)
*C12C 5/04* (2006.01)
*A01N 25/00* (2006.01)
*A01N 65/00* (2009.01)

(52) U.S. Cl. .............. 424/195.17; 514/777; 426/98; 426/540

(58) Field of Classification Search .......... None
See application file for complete search history.

(56) References Cited

U.S. PATENT DOCUMENTS

| | | | |
|---|---|---|---|
| 3,971,852 A | 7/1976 | Brenner et al. | |
| 5,431,929 A | 7/1995 | Yatka et al. | |
| 2006/0134299 A1* | 6/2006 | Lahteenmaki | ........ 426/590 |
| 2008/0026016 A1 | 1/2008 | Koepsel et al. | |
| 2008/0075805 A1 | 3/2008 | Dorr et al. | |

FOREIGN PATENT DOCUMENTS

| | | |
|---|---|---|
| JP | 3-197409 A | 8/1991 |
| JP | 4-262757 A | 9/1992 |
| JP | 10-179025 A | 7/1998 |
| JP | 2001-186858 A | 7/2001 |
| JP | 3302999 B2 | 5/2002 |
| JP | 2003-55688 A | 2/2003 |
| JP | 3510552 B2 | 1/2004 |
| JP | 2004-300094 A | 10/2004 |
| JP | 2004-339158 A | 12/2004 |
| JP | 2006-87 A | 1/2006 |
| WO | WO-93/04598 A1 | 3/1996 |
| WO | WO-01/32038 A1 | 5/2001 |
| WO | WO-2004/008872 A2 | 1/2004 |
| WO | WO-2006/000347 A1 | 1/2006 |
| WO | WO-2006/007993 A1 | 1/2006 |

OTHER PUBLICATIONS

Niness, K.R. (1999) Inulin and oligofructose: What are they? J. Nutr. 129: 1402S-1406S.*
A. Franck., "Technological functionality of insulin and oligofructose", British Journal of Nutrition, 2002, vol. 82, Suppl. 2, pp. S287-S291.

* cited by examiner

*Primary Examiner* — Chris R Tate
*Assistant Examiner* — Russell Fiebig
(74) *Attorney, Agent, or Firm* — Birch, Stewart, Kolasch & Birch, LLP

(57) ABSTRACT

A powder composition of a functional oil material is obtained by drying an emulsion composition comprising at least one functional oil component and (i) at least one water-soluble encapsulating agent selected from saccharide containing at least two sugar units including a fructose unit or (ii) at least one water-soluble encapsulating agent selected from saccharides containing at least one galactose unit and one fructose unit. Food compositions, cosmetic compositions and pharmaceutical compositions are provided which contain the powder composition described above.

12 Claims, No Drawings

POWDER COMPOSITION, METHOD FOR PRODUCING THE SAME, AND FOOD COMPOSITION, COSMETIC COMPOSITION AND PHARMACEUTICAL COMPOSITION CONTAINING THE SAME

TECHNICAL FIELD

The present invention relates to a powder composition, a method for producing the same, and a food composition containing the powder composition, a cosmetic composition containing the powder composition and a pharmaceutical composition containing the powder composition. In particular, it relates to a powder composition containing a functional oil component, a method for producing the same, and a food composition containing the powder composition, a cosmetic composition containing the powder composition and a pharmaceutical composition containing the powder composition.

BACKGROUND ART

An oil component has conventionally been added to drinks, foods, cosmetics, pharmaceutical products and the like. However, the oil component is insoluble or scarcely-soluble in water. For this reason, the oil component has generally been mixed as a so-called emulsion with an aqueous medium by using a certain emulsification means. An emulsion scatters light depending on its particle diameter. Therefore, the emulsion and foods and cosmetics having the emulsion added thereto are turbid, and the turbidity may be not preferred on appearance. As a result, it has been desired to decrease the particle diameter of the emulsion to such an extent that light scattering becomes insignificant. Furthermore, the emulsion is generally in a semi-stable state, and has had great problems in that the particle diameter is increased during storage to cause separation of the water phase and the oil phase during long-term storage.

On the other hand, in recent years, many commercial products such as foods and cosmetics containing various nutritionally functional materials are present, accompanying the boom in healthcare commercial products. Even in the commercial products, such as foods and cosmetics, it has become apparent that if the commercial products contain lipid-soluble nutritionally functional materials that are insoluble or scarcely-soluble in water, there are various problems in, for example, deterioration of materials themselves and demulsification during storage as described above.

A method in which a powdered composition is formed through a step of drying an emulsion has been proposed as a method that enables handling of the oil component in more stable state (see, for example, Japanese Patent Application Laid-Open (JP-A) No. 2003-55688). Powderization is a desirable method in the points of improvement of storability due to removal of water, reduction of transportation costs, improvement of handling properties, and the like.

A known use of general-purpose powdered compositions is powder oils and fats, and application examples thereof include bakery goods, frozen foods, western confectionery, Japanese confectionery, fried goods and noodle goods. Flavor (perfume) is known as another example of use, and application examples thereof include chewing gums, powdered drinks, powdered desserts, various toiletry goods and fibers.

JP-A No. 4-262757 discloses a method of powderizing including (i) emulsifying an edible oil material using a film-forming agent containing a mixture of a highly degradable dextrin and a sucrose fatty acid ester, and then (ii) drying. Japanese Patent No. 3302999 discloses a carotenoid composition for foods. The carotenoid composition contains an oil solvent containing carotenoid, a water-dispersible matrix, a stabilizer and a natural emulsifier. In the patent, sucrose, glucose, fructose, mannose, pentose, maltose and maltodextrin are disclosed as matrix materials. Japanese Patent No. 3510552 discloses that, in addition to excipients such as gum arabic, modified starch and cyclodextrin, palatinose or raffinose is added in order to improve perfume retainability and stability against oxidation of perfume powder.

DISCLOSURE OF INVENTION

However, when a powdered composition is formed for long-term storage, it is necessary to secure transparency and storage stability of a colorant at the time the powder composition is redissolved, but the above techniques are still insufficient from the standpoints of transparency and stability of a colorant.

Accordingly, an object of the present invention is to provide a powder composition that is superior in transparency and colorant storage stability even after redissolution, a food composition using the powder composition, a cosmetic composition using the powder composition and a pharmaceutical composition using the powder composition.

According to an aspect of the present invention, there is provided a powder composition of a functional oil material obtained by drying an emulsion composition including at least one functional oil component and at least one water-soluble encapsulating agent (A) selected from saccharides containing at least two sugar units including a fructose unit. When the powder composition is dissolved to form a 1% by mass aqueous solution, the average particle diameter of the resultant emulsion particles is preferably from 10 nm to 500 nm.

The powder composition may include at least one emulsifier selected from sucrose fatty acid esters, polyglycerin fatty acid esters and lecithins. The water-soluble encapsulating agent is preferably a saccharide having from 2 to 60 fructose units.

In the powder composition, the functional oil material may be a carotenoid colorant.

According to another aspect, there is provided a method for producing a powder composition. The method is a method for producing a powder composition containing a functional oil material, and includes (i) emulsifying at least one functional oil component in an aqueous medium in the presence of at least one emulsifier selected from sucrose fatty acid esters, polyglycerin fatty acid esters and lecithins to obtain an emulsion composition, (ii) adding at least one water-soluble encapsulating agent (A) selected from saccharides containing at least two sugar units including a fructose unit to the aqueous medium and/or the emulsion composition, and (iii) drying the emulsion composition containing the water-soluble encapsulating agent (A).

According to other aspects, there are provided a food composition, a cosmetic composition and a pharmaceutical composition, each including the above-mentioned powder composition.

According to these aspects, it is possible to provide a powder composition that is superior in transparency and colorant storage stability even after redissolution, and a food composition, a cosmetic composition and a pharmaceutical composition, each using the powder composition.

From another viewpoint, when a powdered composition is formed for long-term storage, it is necessary to secure transparency of a colorant at the time the powder composition is redissolved. Further, it has been difficult to secure both of (i)

a high yield in the drying step in the production process, in particular reduction of the loss caused by adhesion to inside of the apparatus at the time of spray drying, and (ii) transparency at the time of redissolution.

Accordingly, another object of the present invention is to provide a powder composition which contains a functional oil component and which achieves transparency after redissolution and a high yield during the drying step, a food composition using the powder composition, a cosmetic composition using the powder composition and a pharmaceutical composition using the powder composition.

According to another aspect of the invention, there is provided a powder composition of a functional oil material obtained by drying an emulsion composition including at least one functional oil component and at least one water-soluble encapsulating (B) agent selected from saccharides containing at least one galactose unit and one fructose unit. When the powder composition is dissolved to form a 1% by mass aqueous solution, the average particle diameter of the resultant emulsion particles is preferably from 10 nm to 500 nm.

In the powder composition, the water-soluble encapsulating agent (B) is preferably a saccharide having 2 to 60 sugar units, and may be at least one selected from raffinose and stachyose.

The powder composition may include at least one emulsifier selected from sucrose fatty acid esters, polyglycerin fatty acid esters and phospholipids.

In the powder composition, the functional oil material may be a carotenoid colorant.

According to another aspect, there is provided a method for producing a powder composition. The method is a method for producing a powder composition containing a functional oil material, and includes (i) emulsifying at least one functional oil component in an aqueous medium, in the presence of at least one emulsifier selected from sucrose fatty acid esters, polyglycerin fatty acid esters and phospholipids to obtain an emulsion composition, (ii) adding to the aqueous medium and/or the emulsion composition at least one water-soluble encapsulating agent (B) selected from saccharides containing at least one galactose unit and one fructose unit, and (iii) drying the emulsion composition containing the water-soluble encapsulating agent (B).

According to other aspects, there are provided a food composition, a cosmetic composition and a pharmaceutical composition, each including the above-mentioned powder composition.

According to the aspects described, it is possible to provide a powder composition which contains a functional oil component and which achieves transparency after redissolution and a high yield during the drying step, and a food composition, a cosmetic composition and a pharmaceutical composition, each using the powder composition.

BEST MODE FOR CARRYING OUT THE INVENTION

The powder composition according to a first embodiment is a powder composition of a functional oil material obtained by drying an emulsion composition including at least one functional oil component and at least one water-soluble encapsulating agent (A) selected from saccharides containing at least two sugar units including a fructose unit.

The powder composition according to the first embodiment contains a specific water-soluble encapsulating agent (A), and therefore can protect oil droplets in the course of powderization and during storage of the powder. Additionally, when the powder composition is redissolved, water dispersibility of the functional oil component can be superior. As a result, even after redissolved, the powder composition can maintain good transparency and good colorant stability.

The powder composition according to a second embodiment is a powder composition of a functional oil material obtained by drying an emulsion composition including at least one functional oil component and at least one water-soluble encapsulating agent (B) selected from saccharides containing at least one galactose unit and one fructose unit.

The powder composition according to the second embodiment contains a specific saccharide as a water-soluble encapsulating agent (B), and therefore is excellent in the drying property at the time of spray drying, can protect oil droplets in the course of powderization and during storage of the powder, and can provide excellent water-dispersibility of the functional oil component when the powder composition is redissolved. As a result, the loss due to adhesion to the apparatus at the time of spray drying very small, and satisfactory transparency can be maintained even after the powder composition is redissolved.

In the following, common descriptions to the first and second embodiments are given.

(a) Functional Oil Component

The functional oil component used in the invention means an oil component which exhibits useful effect when used in foods, cosmetics and pharmaceutical products. In terms of a chemical structure, examples of the functional oil component include oils and fats, hydrocarbons, waxes, esters, fatty acids, higher alcohols, polymers, oil-soluble colorants and oil-soluble proteins. Examples further include various plant-derived oils and various animal-derived oils, which are mixtures of the above-illustrated materials. However, the invention is not particularly limited to the above-mentioned examples.

From the function of the functional oil component, examples thereof include, but are not limited to, ultraviolet absorbers, antioxidants, anti-inflammatory agents, moisturizers, hair-protecting agents, dispersing agents, solvents, whitening agents, anti-spots, cellular stimulants, emollient agents, keratolytic agents, antistatic agents, vitamins, metabolic syndrome improving agents, antihypertensives and sedatives.

Examples of preferred functional oil components that can be used in the invention include carotenoids, vitamin Es (tocopherol, tocotrienol and the like), ubiquinones, and ω-3 oils and fats (oils and fats containing EPA, DHA, linolenic acid and the like).

In the invention, when a carotenoid colorant, which is a oil-soluble functional colorant, is used as a functional oil component, a powder composition can be obtained which shows remarkable effects in high transparency and superior storage stability when dispersed in water.

Preferred examples of carotenoids in the invention include carotenoids containing natural colorants, and examples of the natural colorants include colorants of terpenoids of from yellow to red derived from plants, algae and bacteria.

The carotenoids are not limited to naturally-occurring carotenoids, and any carotenoids obtained by usual methods can be used in the invention. For example, many of the carotenes described below in the explanation of carotenoids are produced also by synthesis, and many of commercially-available β-carotenes are synthetically produced.

Examples of the carotenoids include hydrocarbons (carotenes) and their oxidized alcohol derivatives (xanthophylls). Examples thereof include actinioerythrol, astaxanthin, bixin, kantaxanthin, capxanthin, capsorbin, β-8'-apo-carotenal (apocarotenal), β-12'-apo-carotenal, α-carotene, β-carotene, "carotene" (a mixture of α- and β-carotenes), γ-carotene, β-cryptoxanthin, echinenone, lutein, lycopene, violerythrin, zeaxanthin and esters of compounds having a hydroxyl or carboxyl group selected from the above.

Many carotenoids are naturally present in the form of cis- and trans-isomers, but synthesized products are often a racemic mixture. In general, carotenoids can be extracted from plant materials. Those carotenoids have various functions. For example, lutein extracted from petal of *calendula* is widely used as a raw material for poultry feed, and has the function of coloring poultry skin and fat, and poultry eggs.

The carotenoids used in the invention are preferably oily at ordinary temperature from the standpoint of making the emulsion particle diameter very small. In a preferable example, it is possible to include at least one selected from astaxanthin and astaxanthin derivatives (hereinafter generically referred to as "astaxanthins") such as esters of astaxanthin, which have antioxidant effects, anti-inflammatory effects, skin antiaging effects, whitening ability and the like and which are known as yellow to red colorants. These astaxanthins are more preferably products extracted from natural materials by using supercritical carbon dioxide gas, from the point of odor when powder is formed.

Astaxanthin is a red colorant having an absorption maximum at 476 nm (ethanol), 468 nm (hexane), and belongs to xanthophylls—one kind of carotenoid (Davies, B. H.: In "Chemistry and Biochemistry of Plant Pigments", T. W. Goodwin ed., 2nd ed., 38-165, Academic Press, NY, 1976). The chemical structure of astaxanthin is 3,3'-dihydroxy-β,β-carotene-4,4'-dione ($C_{40}H_{52}O_4$ with a molecular weight of 596.82).

Astaxanthin has three isomers of 3S,3S'-form, 3S,3R'-form (meso form) and 3R,3R'-form, which differ in the steric configurations of the hydroxyl groups at 3 (3')-position of the ring structures present at both ends of the molecule. Additionally, cis- and trans-isomers of a conjugated double bonds at the molecular center are also present. For example, there are all cis- and 9-cis and 13-cis forms of isomer.

The hydroxyl group at a 3(3')-position can form an ester with a fatty acid. The astaxanthin obtained from krill is a diester having two fatty acids bonded thereto (Yamaguchi, K., Miki, W., Toriu, N., Kondo, Y., Murakami, M., Konosu, S., Satake, M., and Fujita, T.: The composition of carotenoid pigments in the antrarctic krill Euphausia superba, Bull. Jap. Sos. Sci. Fish., 1983, 49, p. 1411-1415). The astaxanthin obtained from *H. pluvialis* has a 3S, 3 S'-form and contains a large amount of a monoester having one fatty acid bonded thereto (Renstrom, B., Liaaen-Jensen, S.: Fatty acids of some estrified carotenols, Comp. Biochem. Physiol. B, Comp. Biochem., 1981, 69, p. 625-627).

Furthermore, the astaxanthin obtained from *Phaffia Rhodozyma* has a 3R,3R'-form (Andrewes, A. G., Starr, M. P.: (3R,3'R)-Astraxanthin from the yeast Phaffarhodozyma, Phytochem., 1976, 15, p. 1009-1011), and has the opposite structure to the 3S,3S'-form, which is a usual form found in the nature. This astaxanthin is present in a free form which does not form an ester with a fatty acid (Andrewes, A. G, *Phaffia*, H. J., Starr, M. P.: Carotenids of *Phaffia rhodozyma*, a red pigmented fermenting yeast, Phytochem., 1976, 15, p. 1003-1007).

Astaxanthin and its ester forms were first separated from a lobster (*Astacus gammarus* L.) by R. Kuhn et al., and its estimated structure was disclosed (Kuhn, R., Soerensen, N. A.: The coloring matters of the lobster (*Astracus gammarus* L.), Z. Angew. Chem., 1938, 51, p. 465-466). Since then, it has been clarified that astaxanthin is widely distributed in nature, is generally present in an astaxanthin fatty acid ester form, and is also present, in crustacean, in the form of an astaxanthin protein (ovorubin and crustacyanin) in which astaxanthin is bonded to a protein (Cheesman, D. F.: Ovorubin, a chromoprotein from the eggs of the gastropod mollusc *Pomacea canaliculata*, Proc. Roy. Soc. B, 1958, 149, p. 571-587).

The astaxanthin and/or its ester (astaxanthins) may be contained in the emulsion composition according to the invention in the form of an astaxanthin-containing oil separated and extracted from natural products containing astaxanthin and/or an astaxanthin ester. Examples of such an astaxanthin-containing oil include extracts, such as extracts extracted from a culture of red yeast *Phaffia*, green alga *Haematococcus*, marine bacteria or the like and extracts from antarctic krill and the like.

It is known that *Haematococcus alga* extracts (colorant derived from *Haematococcus algae*) differ from a colorant derived from krill and a synthesized astaxanthin in the kind of the ester and its content.

Astaxanthins usable in the invention include the above extracted products (extracts), products obtained by appropriately purifying the extracts as necessary, and synthetic products. As the astaxanthins, products extracted from *Haematococcus algae* (hereinafter sometimes referred to as "*Haematococcus alga* extract") are particularly preferred from the viewpoints of quality and productivity.

Specifically, *Haematococcus alga* extracts used in the invention may derive from the following: *Haematococcus pluvialis*, *Haematococcus lacustris*, *Haematococcus capensis*, *Haematococcus droebakensis* and *Haematococcus zimbabwiensis*.

Various methods may be used as methods for culturing *Haematococcus alga* that can be used in the invention, such as the methods disclosed in JP-A No. 8-103288. The methods are not particularly limited, as long as the cells have undergone morphological change from vegetative cells to cyst cells, which are as dormant cells.

*Haematococcus alga* extracts that can be used in the invention may be obtained by crushing, as required, cell walls of the above raw materials by a method described in, for example, JP-A No. 5-68585 and adding an extracting solvent such as carbon dioxide in a supercritical state or an organic solvent such as acetone, ether, chloroform or alcohol (e.g., ethanol, methanol), followed by extraction.

The *Haematococcus alga* extracts may include, like the colorants described in JP-A No. 2-49091, astaxanthin or an ester of astaxanthin as a colorant pure component, and may include an ester of astaxanthin in an amount of at least 50% by mol in general, preferably at least 75% by mol, and more preferably at least 90% by mol.

In the invention, commercially available *Haematococcus alga* extracts may be used, and examples thereof include ASTOTS-S, ASTOTS-2.5 O, ASTOTS-5 O and ASTOTS-10 O, manufactured by Takedashiki Co., Ltd.; AstaREAL oil 50F and AstaREAL oil 5F manufactured by Fuji Chemical Industry Co., Ltd.; BioAstin SCE7 manufactured by Toyo Koso Kagaku Co., Ltd.; and astaxanthin PURESTA manufactured by Yamaha Motor Co., Ltd.

In the invention, the content of astaxanthins as a colorant pure component in *Haematococcus alga* extract is preferably from 0.001% to 50% by mass, and more preferably from 0.01% to 25% by mass, from the viewpoint of extraction cost.

In the invention, there are cases where synergy effects are obtained by combining functional oil components having different functions. For example, an emulsion composition containing a combination of a carotenoid and a vitamine E (a tocopherol) is particularly preferable in terms of antioxidant power.

Tocopherols are selected from a group of compounds consisting of tocopherol and its derivatives. Examples of the group of compounds selected from tocopherol and its derivatives include dl-α-tocopherol, dl-β-tocopherol, dl-γ-tocopherol, dl-δ-tocopherol, dl-α-tocopherol acetate, dl-α-tocopherol nicotinate, dl-α-tocopherol linoleate, dl-α-tocopherol succinate, α-tocotrienol, β-tocotrienol, γ-tocotrienol and δ-tocotrienol. These compounds are frequently used in the state of a mixture, and can be used in the state called "extracted tocopherol", "mixed tocopherol" and the like. The content of tocopherol with respect to carotenoid in the emulsion composition according to the invention is not particularly limited. However, the ratio of the amount of tocopherol to the amount of carotenoid is preferably within the range from 0.1 to 5, more preferably from 0.2 to 3, and further preferably from 0.5 to 2.

Examples of other preferred functional oil components than carotenoid colorants include ubiquinones, particularly coenzyme Q10. In Japan, coenzyme Q10 was first approved and sold as medical drug of metabolic cardiacs in 1974. Since then, coenzyme Q10 including OTC (over the counter) medicine has been treated as medical drugs. On the other hand, in overseas (mainly Europe and USA), demand for the coenzyme Q10 as healthy food materials having high effectiveness and safety has been increased for over ten years. In Japan, coenzyme Q10 was listed in "Component essence (raw material) which is recognized as foods unless pharmaceutical effect-efficacy is claimed" in Notice by Director General, Pharmaceutical Bureau, Ministry of Health, Labor and Welfare, 2001 "Revision of standard regarding a scope of drugs" (Issuance No. 243), and relaxation of regulations was made such that coenzyme Q1 may be treated as food. In Japan, attention is paid to versatile functions that this food material possesses, and many general foods containing coenzyme Q10 (so-called healthy food) are being commercialized.

In order to utilize the function that coenzyme Q10 possesses, it is important to render water-solubility to this material, which is a lipid-soluble material. In the powder composition according to the invention, the functional oil component is protected in a good state. Therefore, it is possible to maintain a small particle diameter when the powder is redispersed in water, to realize a superior transparency of the liquid, and to allow the powder to be sufficiently absorbed in a living body. As a result, when the invention is applied, good performance that is no worse than that of an emulsion formulation can be obtained.

Other preferable examples of the functional oil component in the invention include ω(omega)-3 oils and fats of unsaturated fatty acids having a double bond at ω-3 position. Examples of the ω(omega)-3 oils and fats include linolenic acid, eicosapentaenoic acid (EPA), docosahexaenoic acid (DHA), and fish oils containing those.

Among those, DHA is an abbreviation of docosahexaenoic acid and is a general name for carboxylic acids (22:6) having a chain of 22 carbons containing 6 double bonds. Usually, DNA has cis-double bonds at all of 4, 7, 10, 13, 16 and 19-positions, which are important for a living body.

In general, a lot of DHA is contained in fish oils, and is added to supplements, confectioneries and the like with a catchword like "getting healthy" and "becoming clever" when ingested. DHA is a major component of fatty acids contained in phospholipid of semen, brain and retina. Ingestion of DHA decreases the amount of neutral fat in the blood, thereby reducing risk of heart decease. Furthermore, there is a report saying that when DHA is deficient, the amount of serotonin in the brain is decreased, thereby inducing hyperactivity disorder. It is also said that ingestion of DHA is effective to such diseases as Alzheimer's dementia and depression.

A large proportion of DHA contained in fishes and other organisms is produced by a process in which DNA produced by genus *Schizochytrium* (a kind of microalgae) is concentrated through the course of food chain. Therefore, it is preferred, but is not essential, in the invention to use naturally-derived DHA.

DHA is also included in the scope of oils and fats. Therefore, it is preferred to emulsify DHA, in advance, to form minute oil droplets so as to increase absorption in a living body. Furthermore, it is known that DHA is liable to deteriorate over time during storage, and the flavor is greatly deteriorated by the deterioration of DHA over time. When DHA is contained in the powder composition according to the invention, DHA is protected in good state, and deterioration of oils and fats and deterioration in flavor can be suppressed; additionally, because the powder composition easily dissolves in water, it is possible to widely utilize DHA as a component in an aqueous composition such as soft drink and milk. Furthermore, in the powder composition according to the invention, the content of DHA can be easily made high, and the particle diameter at the time of redispersion in water can be sufficiently small, whereby a satisfactory liquid transparency is achieved.

Other examples of the compound that can be used as the functional oil component include liquid oils (fatty oils), which are liquid at ordinary temperature, and fats, which are solid at ordinary temperature.

Examples of liquid oils include olive oil, camellia oil, macadamia nut oil, castor oil, avocado oil, evening primrose oil, turtle oil, corn oil, mink oil, rapeseed oil, egg yolk oil, sesame oil, persic oil, wheat germ oil, sasanqua oil, linseed oil, safflower oil, cotton seed oil, perilla oil, soybean oil, peanut oil, tea seed oil, kaya oil, rice bran oil, china wood oil, tung oil, hohoba oil, germ oil, triglycerin, glycerin trioctanoate, glycerin triisopalmitate, salad oil, safflower oil, palm oil, coconut oil, peanut oil, almond oil, hazelnut oil, walnut oil, grape seed oil, squalene, and squalane.

Examples of solid fats include beef tallow, hydrogenated beef tallow, neet's-foot tallow, beef bone tallow, mink oil, egg yolk oil, lard, horse fat, mutton tallow, hydrogenated oil, cacao fat, coconut oil, hydrogenated coconut oil, palm oil, palm hydrogenated oil, Japan tallow, Japan tallow kernel oil and hydrogenated castor oil.

Other examples of the functional oil component include hydrocarbons such as liquid paraffin, paraffin, Vaseline, ceresin and microcrystalline wax; waxes such as carnauba wax, candellia wax, jojoba oil, bees wax and lanolin; esters such as isopropyl myristate, 2-octyldedecyl myristate, cetyl 2-ethylhexanoate and diisostearyl malate; fatty acids such as palmitic acid, stearic acid, isostearic acid, linoleic acid and arachidonic acid; higher alcohols such as cetyl alcohol, stearyl alcohol, isostearyl alcohol and 2-octyldodecanol; silicone oils such as methyl polysiloxane and methylphenyl polysiloxane; polymers, oil-soluble colorants, oil-soluble proteins, and various plant-derived oils and animal-derived oils, which are mixtures of substances selected from the above substances.

It is preferable to use two or more functional oil components in combination in order to further increase dispersibility in water. Preferable examples of oil components that can be additionally used for this purpose include DHA, squalene and squalane, and squalene is particularly preferred. In particular, when an oil component that is solid at ordinary temperature like coenzyme Q10 is used, the oil component is particularly preferably used in combination with DHA, squalene, squalane or the like.

The content of the functional oil component in the powder composition according to the invention may be from 0.01 to 50% by mass. The content of the functional oil component in the powder composition is preferably from 0.1 to 30% by mass, and more preferably from 0.3 to 10% by mass from the viewpoints of allowing the component to work effectively and handling properties of the powder.

The content of the functional oil component in the emulsion composition according to the invention is preferably from 0.1 to 10% by mass, more preferably from 0.5 to 5% by mass, and further preferably from 0.5 to 2% by weight, from the standpoints of reduction in the particle diameter of emulsified particles and production efficiency.

(b) Water-soluble Encapsulating Agent (A)

The powder composition according to the first embodiment contains at least one water-soluble encapsulating agent (A) selected from saccharides containing at least two sugar units including a fructose unit.

The water-soluble encapsulating agent (A) according to the first embodiment can protect oil droplets in the course of powderization when drying, and during storage of the powder. As a result, the particle diameter of the oil droplets can be maintained very small, and additionally, deterioration of the functional oil component in the oil droplets can be minimized.

Furthermore, when the powder composition is redissolved in water, the water-soluble encapsulating agent (A) can improve water dispersibility of the functional oil component, and additionally can improve transparency after redissolution.

The saccharide containing at least two sugar units including a fructose unit in the first embodiment (hereinafter simply referred to as "fructose saccharide") refers to a polymer or oligomer which contains fructose as a repeating unit and which is formed by dehydration condensation of plural sugar units. In the first embodiment, a saccharide having less than 20 sugar repeating units including a fructose unit is called a fructose oligomer, and a saccharide having 20 or more sugar repeating units including a fructose unit is called a fructose polymer.

The number of the fructose repeating units is preferably from 2 to 60, and more preferably from 4 to 20, from the standpoint of drying suitability and reduction of the particle diameter of oil droplets at the time of redissolution. When the number of sugar repeating units (degree of polymerization of fructose units) is 2 or more, hygroscopicity is not too strong, and thus the reduction in recovery rate caused by adhesion to a drying container during drying process can be prevented effectively. On the other hand, when the number of the fructose repeating units is 60 or less, increase in the particle diameter of oil droplets at the time of redissolution in water can effectively be prevented.

The fructose saccharide may contain, in addition to fructose, one or more other monosaccharides at the terminal or in the chain of the molecule. Examples of such other monosaccharides that can be contained include, but are not limited to, glucose, galactose, mannose, idose, altrose, gulose, talose, allose, xylose, arabinose, lyxose, ribose, threose, erythrose, erythrulose, xylulose, ribulose, psicose, sorbose and tagatose. Of those monosaccharides, glucose is preferred from the standpoint of easy availability. Furthermore, those monosaccharides are preferably located at a terminal of a fructose chain from the standpoint of reduction in the particle diameter of oil droplets at the time of redissolution.

When other sugars than fructose are contained, their total content in terms of the degree of polymerization may be 50% or less, and preferably 30% or less, with respect to the number of fructose units from the standpoint of drying suitability and reduction in the particle diameter of oil droplets at the time of redissolution.

Inulin is preferable as the water-soluble encapsulating agent (A) used in the first embodiment, from the standpoint of storage stability of a colorant and ease of availability. Inulin in the first embodiment refers to a fructose saccharide having one glucose at a terminal thereof. It is known that inulin is widely present in nature, and inulin is contained in large amount in chicory, Jerusalem artichoke, dahlia, garlic, leek, onion and the like. The detail of inulin is described in Handbook of Hydrocolloids, G. O. Phillips, P. A. Williams Ed., 397-403, (2000) CRC Press. In general, a glucose unit is represented by G, and a fructose unit is represented by F, when expressing a chain length. Sucrose, represented by GF, is not contained in the inulin in the first embodiment.

Inulins extracted from nature are, in general, GF2 (kestose), GF3 (nystose), polymers or oligomers of from GF4 (fructosylnystose) to about GF60, or their mixtures.

In the first embodiment, inulin may be a commercially available product obtained by separating inulin, by hot water extraction, from roots of chicory, Jerusalem artichoke, dahlia or the like, concentrating the resultant aqueous solution, and powderizing the concentrated aqueous solution by spray-drying. Examples thereof include FRUTAFILT extracted from chicory root (manufactured by SENSUS), BENEO extracted from chicory root (manufactured by ORAFTI), dahlia root-derived reagent (manufactured by Wako Pure Chemical Industries, Ltd., and SIGMA) and chicory root-extracted reagent (manufactured by SIGMA).

The scope of fructose saccharide in the first embodiment encompasses products prepared from sucrose by utilizing fructan transfer activity of β-fructofuranosidase. Examples of the product include Fuji FF (manufactured by Fuji Nippon Seito Corporation) and GF2 (manufactured by Meiji Seika Kaisha, Ltd.).

Inulin used in the first embodiment preferably has a fructose repeating number (degree of polymerization) of from 2 to 60, from the standpoint of reduction of the particle diameter of oil droplets at the time of redissolution. The fructose repeating number (degree of polymerization) is more preferably from 4 to 20 from the standpoints of adhesion to an apparatus at the time of spray drying and solubility in water.

It is preferred that the fructose saccharide according to the first embodiment is added at the time of emulsification or is added before emulsification. However, it is possible that a part or the whole of the fructose polymer or fructose oligomer is added after emulsification.

According to need, in combination with the above-described fructose saccharide, another water-soluble polymer or oligomer may be used for the water-soluble encapsulating agent (A). Examples of such an additional water-soluble polymer or oligomer include, but are not limited to, agarose, starch, dextrin, maltodextrin, carrageenan, gelatin, xanthan gum, gellan gum, galactomannan, gum arabic, pectin, casein, tragand gum, xyloglucan, β-glucan, curdlan, water-soluble soybean fiber, chitosan and alginic acid.

The content of the water-soluble encapsulating agent (A) in the first embodiment is, in the case of an emulsion composition, preferably from 1 to 20 times the mass of the oil phase containing the functional oil component, and particularly preferably from 2 to 10 times the mass of the oil phase containing the functional oil component, from the viewpoints of handling properties of the powder obtained and production efficiency. Furthermore, in the case of a powder composition, the content of the water-soluble encapsulating agent (A) is preferably from 30 to 95% by mass, and more preferably from 50 to 80% by mass, based on the whole mass of the powder composition.

When the fructose saccharide is used in combination with one or more other water-soluble polymers and/or oligomers, the total blending amount of the fructose saccharide is from 50 to 100% by mass, and preferably from 70 to 100% by mass, based on the whole amount of the water-soluble encapsulating agent (A) from the standpoint of reduction of the particle diameter of oil droplets at the time of redissolution.

(b') Water-soluble Encapsulating Agent (B)

The powder composition according to the second embodiment includes at least one water-soluble encapsulating agent (B) selected from saccharides containing at least one galactose unit and one fructose unit.

The water-soluble encapsulating agent (B) in the second embodiment exhibits excellent non-hygroscopic property, so that an emulsion composition can be dried appropriately. As a result, the adhesion amount to the wall surface of a production apparatus in the drying step can be made small. In addition, the oil droplets can be protected during powderizing process in drying and during storage of the powder. As a result, the particle diameter of oil droplets can be maintained small, and superior transparency can be obtained when the powder composition is redissolved in water.

The saccharide containing at least one galactose unit and one fructose unit in the second embodiment (hereinafter simply referred to as "galactose/fructose-containing saccharide") refers to a polymer or oligomer which includes galactose and fructose as repeating units and which is formed by dehydration condensation of plural sugar units. In the second embodiment, those having less than 20 sugar repeating units (sometimes simply called "sugar units" in the present specification) are called oligosaccharides (oligomers), and those having 20 or more sugar repeating units are called polysaccharides (polymers). In the second embodiment, this nomenclature applies to other oligomers and polymers containing other repeating units.

When the number of the sugar repeating units is two, there are one galactose unit and one fructose unit. When the number of the sugar repeating units is three, there are two galactose repeating units and one fructose unit. The number of the sugar repeating units is preferably from 2 to 60, more preferably from 3 to 15 from the viewpoints of drying suitability and reduction of the particle diameter of oil droplets at the time of redissolution. When the number of repeating units (the polymerization degree of sugar) is two or more, the hygroscopic property is not excessive, and reduction of recovery rate caused by adhesion to a drying container during the drying process can be effectively prevented. On the other hand, when the number of repeating units is sixty or less, increase in the particle diameter of oil droplets at the time of redissolution in water can be effectively prevented.

The saccharide containing a galactose unit and a fructose unit may include, in addition to the above sugar units, one or more other monosaccharides at a terminal or in the chain of the molecule. Examples of such other monosaccharides that can be contained include, but are not limited to, glucose, mannose, idose, altrose, gulose, talose, allose, xylose, arabinose, lyxose, ribose, threose, erythrose, erythrulose, xylulose, ribulose, psicose, sorbose and tagatose. Among these monosaccharides, glucose is preferable from the viewpoint of easy availability. The additional monosaccharides may be located between galactose and fructose, or may be located at a terminal; the additional monosaccharides are preferably located between galactose and fructose in view of yield of the drying step.

When additional saccharides other than galactose and fructose are contained, their total content with respect to the sum of the galactose units and the fructose units may be, in terms of polymerization degree, 50% or less, and is preferably 30% or less, from the viewpoints of drying suitability and reduction in the particle size of oil droplets at the time of redissolution.

The water-soluble encapsulating agent (B) is preferably raffinose, stachyose or verbascose from the viewpoints of yield at drying and transparency at redissolution. In particular, raffinose is more preferable from the viewpoints of transparency at the time of being dispersed in water and ease of availability, and stachyose and verbascose are more preferable from the viewpoint of yield at drying.

Raffinose in the second embodiment is a trisaccharide containing one D-galactose unit, one D-glucose unit and one D-fructose unit. Raffinose is known to be present widely in nature, and is contained in a relatively large amount in beet, eucalyptus tree sap, soy bean, cabbage, broccoli, asparagasu and the like.

In the second embodiment, raffinose may be a commercially available product obtained by separating raffinose from beat or the like by hot water extraction, concentrating the resultant aqueous solution and spray drying the concentrated aqueous solution to form powder. Examples thereof include raffinose (manufactured by Nippon Beat Sugar Manufacturing Co., Ltd.).

Stachyose is a tetrasaccharide consisting of a series D-fructose, D-galactose, D-galactose and D-glucose, and, in the natural world, stachyose is contained in a relatively large amount in beans (e.g., soy bean) and cucurbitaceous plants. An example of commercially available stachyose is SFS oligosaccharide manufactured by Garyu Honpo, Westone Co., Ltd.

Verbascose is a pentasaccharide consisting of a series of D-galactose, D-galactose, D-galactose, D-glucose and D-fructose (in this order), and is contained in beans such as broad bean.

Stachyose and verbascose may be, similarly to raffinose, hot-water extracted from plants, and the resultant aqueous solution may be concentrated and then spray-dried to form powder.

In the second embodiment, the galactose/fructose-containing saccharide is preferably added during or before emulsification. However, it is also possible to add a part or all of the galactose/fructose-containing saccharide after emulsification.

According to need, in combination with the galactose/fructose-containing saccharide, one or more other water-soluble compounds and/or polymers may be used for the water-soluble encapsulating agent (B).

Examples of such additional water-soluble compounds and polymers include, but are not limited to, agarose, starch, dextrin, maltodextrin, inulin, carrageenan, gelatin, xanthan gum, gellan gum, galactomannan, gum arabic, pectin, casein, tragand gum, xyloglucan, β-glucan, curdlan, water-soluble soybean fiber, chitosan and alginic acid.

In the second embodiment, in the case of an emulsion composition, the amount (mass) of water-soluble encapsulating agent (B) contained is preferably 1 to 20 times the mass of the oil phase containing the functional oil component from the viewpoints of production efficiency of the powder composition and transparency, and is preferably 2 to 10 times the mass of the oil phase containing the functional oil component particularly from the viewpoints of the handling property of the obtained powder and production efficiency. Similarly, in the case of a powder composition, the amount of water-soluble encapsulating agent (B) contained is preferably from 30 to 95% by mass, more preferably from 50 to 80% by mass, with respect to the total mass of the powder composition. When the content of the water-soluble encapsulating agent (B) is set to a relatively high content within the above-mentioned range, the yield of the drying step can be heightened. When the content of the water-soluble encapsulating agent (B) is set to a relatively low content within the above-mentioned range, powder containing the functional oil component at a high concentration can be produced.

When the galactose/fructose-containing saccharide is used in combination with one or more other water-soluble polymers and/or oligomers, the blending amount of the galactose/frucotse-containing saccharide may be from 50% to 100% by mass with respect to the total amount of the water-soluble encapsulating agent (B) from the viewpoint of reduction of the particle size of oil droplets at the time of redissolution, and is preferably from 70 to 100% by mass with respect to the total amount of the water-soluble encapsulating agent (B).

Explanations common to both embodiments are resumed.

(c) Emulsifier

Because the oil phase in the emulsion composition containing the functional oil component is emulsified in an aqueous medium before powderization, the powder compositions according to the first and second embodiments may contain at least one emulsifier selected from sucrose fatty acid esters, polyglycerin fatty acid esters and phospholipids.

In the sucrose fatty acid ester used in the invention, the fatty acid has preferably 12 or more carbon atoms, and more preferably from 12 to 20 carbon atoms, from the standpoint of interfacial activity. When the fatty acid has 12 or more carbon atoms, there are cases where emulsion particles having a smaller average particle diameter can be formed.

Preferred examples of the sucrose fatty acid ester include sucrose monooleate, sucrose monostearate, sucrose monopalmitate, sucrose monomyristate and sucrose monolaurate are more preferred.

In the invention, only a single sucrose fatty acid ester may be used, or a mixture of plural sucrose fatty acid esters may be used.

Examples of commercially available products of sucrose fatty acid esters include, but are not limited to, RYOTO-sugar ester S-1170, S-1170S, S-1570, S-1670, P-1570, P-1670, M-1695, O-1570, OWA-1570, L-1695 and LWA-1570 manufactured by Mitsubishi-Kagaku Foods Corporation; and DK ester F140, DK ester F-160 and DK ester SS manufactured by Daiichi-Kogyo Seiyaku Co., Ltd.

The polyglycerin fatty acid ester used in the invention is an ester of a polyglycerin having an average polymerization degree of 4 or more (preferably from 6 to 10) and a fatty acid having from 8 to 18 carbon atoms such as caprylic acid, capric acid, lauric acid, myristic acid, palmitic acid, stearic acid, oleic acid and linoleic acid.

Preferred examples of the polyglycerin fatty acid ester include hexaglycerin monopalmitate, hexaglycerin monomyristate, hexaglycerin monolaurate, decaglycerin monooleate, decaglycerin monostearate, decaglycerin monopalmitate, decaglycerin monomyristate and decaglycerin monolaurate.

Only a single polyglycerin fatty acid ester may be used, or a mixture of plural polyglycerin fatty acid esters may be used.

Examples of commercially available products of polyglycerin fatty acid esters include NIKKOL Hexaglyn 1-L, NIKKOL Hexaglyn 1-M, NIKKOL Decaglyn 1-L, NIKKOL Decaglyn 1-M, NIKKOL Decaglyn 1-SV, NIKKOL Decaglyn 1-50SV, NIKKOL Decaglyn 1-ISV, NIKKOL Decaglyn 1-O, NIKKOL Decaglyn 1-OV and NIKKOL Decaglyn 1-LN manufactured by Nikko Chemicals Co., Ltd.; RYOTO-polyglyester L-7D, L-10D, M-10D, M-7D, P-8D, S-28D, S-24D, SWA-20D, SWA-15D, SWA-10D and O-15D manufactured by Mitsubishi-Kagaku Foods Corporation; and POEM J-0381V and POEM J-0021V manufactured by Riken Vitamin Co., Ltd.

The phospholipid used in the invention includes a glycerin skeleton, a fatty acid residue and a phosphoric acid residue as essential constituents, to which a base, a polyhydric alcohol and the like are optionally bonded; the photopholipid is also called a lecithin.

Examples of the phospholipid that can be used in the invention include glycerolecithins such as lecithin, phosphatidic acid, phosphatidylglycerin, phosphatidylinositol, phosphatidylethanolamine, phosphatidylmethylethanolamine, phosphatidylcholine, phosphatidylserine, bisphosphatidic acid, and diphosphatidylglycerin (cardiolipin); and sphingolecithins such as sphingomyelin. Further examples include lecithins derived from plants such as from soybean, corn, peanuts, rapeseed and wheat; lecithins derived from animals such as egg yolk and cow; and lecithins derived from microorganisms such as *Bacillus coli*, all of which contain a phospholipid component such as those described above. The origin of those phospholipids is not particularly limited, and plant oils such as soybean oil, products derived from animals such as egg yolk, and the like can be used. Purified products are particularly preferred.

The phospholipid has a hydrophilic group and a hydrophobic group in the molecule, and therefore is conventionally used widely as an emulsifier in food, medicine and cosmetic fields. Industrially, phospholipid having purity of 60% or more is used as lecithin, and can be used in the invention. However, from the standpoints of formation of oil droplets having very small particle diameter and stability of the functional oil component, what is generally called a high purity lecithin is preferable, and the high purity lecithin may have a lecithin purity of 80% by mass or more, and more preferably 90% by mass or more.

Examples of the lecithin include various conventional products extracted and separated from living bodies of plants, animals and microorganisms.

In the invention, usable lecithins include not only the above high purity lecithins, but also hydrogenated lecithins, enzymatically decomposed lecithins, enzymatically decomposed, hydrogenated lecithins and hydroxylecithins. The hydrogenated or hydroxylated lecithin is particularly preferred in cosmetic applications. The hydrogenation is conducted by, for example, allowing lecithin to react with hydrogen in the presence of a catalyst, whereby an unsaturated bond in the fatty acid moiety is hydrogenated. By the hydrogenation, oxidation stability of lecithin is improved.

Furthermore, the hydroxylation involves hydroxylation of an unsaturated bond in the fatty acid moiety by heating lecithin together with hydrogen peroxide of high concentration and an organic acid such as acetic acid, tartaric acid or butyric acid. By the hydroxylation, the hydrophilicity of lecithin is improved.

With respect to the phospholipids that can be used in the invention, only a single phospholipid may be used, or a mixture of plural phospholipids may be used.

It is possible to use only a single emulsifier, but it is preferable to use two, or three or more, emulsifiers. Although it is preferred to combine emulsifiers belonging to the same series, the following are also preferable: (i) use of a sucrose fatty acid ester and a polyglycerin fatty acid ester in combination, (ii) use of a sucrose fatty acid ester, a polyglycerin fatty acid ester and a lecithin in combination.

The total amount of emulsifier to be used in the invention may be in a range of from 10 to 1,000% by mass based on the oil phase containing the functional oil component. From the points of reduction of the size of emulsion particles and foaming, the amount is preferably from 50 to 800% by mass, and particularly preferably from 80 to 500% by mass. When the amount falls within the above range, emulsion stability of the emulsion composition can be made satisfactory.

Furthermore, in the invention, one or more other emulsifiers may be contained in addition to the above emulsifier. Examples of such additional emulsifiers include anionic, cationic, nonionic and amphoteric surfactants. Above all, a nonionic surfactant is preferred from the standpoint of emulsion stability.

The surfactant in the invention has an HLB of preferably 10 to 19, more preferably 12 to 17, from the standpoint of emulsion stability The HLB used herein is the balance of hydrophilicity-hydrophobicity generally used in the field of surfactants, and a generally used calculation formula, such as Kawakami's equation, can be used. The following Kawakami's equation is adopted in the invention.

$$HLB=7+11.7 \log(M_w/M_o)$$

In the equation, $M_w$ is the molecular weight of the hydrophilic group, and $M_o$ is the molecular weight of the hydrophobic group.

HLB values described in brochures and the like may be used.

As is apparent from the above formula, a surfactant having a desired HLB value can be obtained by utilizing additive properties of HLB.

Examples of the anionic surfactant include fatty acid soaps such as sodium strearate and triethanolamine palmitate; alkyl ether carboxylic acids and salts thereof; carboxylic acid salts such as a condensate of an amino acid and a fatty acid; alkyl sulfonic acids; sulfonic acid salts such alkene sulfonic acid salts, sulfonic acid salts of fatty acid esters, sulfonic acid salts of fatty acid amides, alkyl sulfonic acid salts and formalin condensates of alkyl sulfonic acid salts; sulfuric acid ester salts such as alkyl sulfuric acid ester salts, secondary higher alcohol sulfuric acid ester salts, alkyl and allyl ether sulfuric acid ester salts, sulfuric acid ester salts of fatty acid esters, sulfuric acid ester salts of fatty acid alkylolamides and sulfuric acid ester salts of turkey red oil or the like; phosphoric acid salts such as alkyl phosphoric acid salts, ether phosphoric acid salts, alkyl allyl ether phosphoric acid salts and amide phosphoric acid salts; and N-acylamino acid-based surfactants.

Examples of the cationic surfactant include amine salts such as alkyl amine salts, polyamines and aminoalcohol fatty acid derivatives; alkyl quaternary ammonium salts, aromatic quaternary ammonium salts, pyridium salts and imidazolium salts.

Examples of the nonionic surfactant include organic acid monoglycerides, sorbitan fatty acid esters, glycerin fatty acid esters, propylene glycol fatty acid esters, polyethylene glycol fatty acid esters, polyglycerin-bonded ricinoleic acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oils, polyoxyethylene hardened castor oils, polyoxyethylene phytostanol ethers, polyoxyethylene phytosterol ethers, polyoxyethylene cholestanol ethers, polyoxyethylene cholesteryl ethers, polyoxyalkylene-modified organopolysiloxanes, polyoxyalkylene/alkyl-comodified organopolysiloxanes, alkanol amides, sugar ethers and sugar amides.

Examples of the amphoteric surfactant include betaine, aminocarboxylic acid salts and imidazoline derivatives.

The surfactant can be appropriately selected from generally sold products. For example, examples of fatty acids include LUNAC series manufactured by Kao Corporation, various fatty acids manufactured by New Japan Chemical Co., Ltd., and various fatty acids manufactured by Nippon Fine Chemical Co., Ltd. Examples of alkyl sulfuric acid salts/polyoxyethylene alkyl ether sulfuric acid salts include EMAL series manufactured by Kao Corporation. Examples of polyoxyethylene alkyl ether acetic acid salts include KAO AKYPO series manufactured by Kao Corporation.

Examples of glycerin fatty acid esters include NIKKOL MGO, NIKKOL DGO, NIKKOL MGS and NIKKOL F series manufactured by Nikko Chemicals Co., Ltd., and EXCEL series manufactured by Kao Corporation. Example of organic acid monoglycerides includes POEM G-002, manufactured by Riken Vitamin Co., Ltd. Examples of sorbitan fatty acid esters include NIKKOL SS series and SO series manufactured by Nikko Chemicals Co., Ltd., and EMASOL series manufactured by Kao Corporation. Example of propylene glycol fatty acid esters includes NIKKOL PMS-SE, manufactured by Nikko Chemicals Co., Ltd.

The amount of surfactant as such an additional emulsifier is preferably from 0.5 time or less, more preferably 2 times or less, further preferably 1.5 times or less, and particularly preferably 1 time or less, the mass of the oil component, from the viewpoint of easily obtaining an emulsion having a very small particle diameter. It is preferred that the amount of the surfactant is 2 times the mass of the oil component or less because problems, such as severe foaming, do not occur.

The addition amount of surfactant as such an additional emulsifier is preferably from 0.01 to 30% by mass, more preferably from 0.1 to 20% by mass, and further preferably from 1 to 15% by mass, based on the mass of the entire powder composition.

An amount of surfactant of 0.01% by mass or more is preferred from the point that interfacial tension between oil phase/water phase in the resultant emulsion composition can easily be made low. Furthermore, an amount of surfactant of 30% by mass or less is preferred from the point that the amount of surfactant is not excessive and problems such as heavy foaming of the emulsion composition hardly occur.

Emulsification for preparing an emulsion composition can be conducted in the presence of an emulsifier. The emulsifier may be added to either of an oil phase and a water phase at a stage prior to emulsification. From the standpoints of formation of finer particles and emulsion stability, it is a preferable method to add plural emulsifiers wherein some of the emulsifiers are added to an oil phase and others are added to a water phase. Furthermore, a part of the emulsifier may be added after emulsification from the standpoint of emulsion stability.

The ratio (mass) of the oil phase to the water phase in the oil-in-water emulsion composition according to the invention is not particularly limited. In general, the oil phase/water phase ratio (% by mass) is preferably from 0.1/99.9 to 50/50, more preferably from 0.5/99.5 to 30/70, and further preferably from 1/99 to 20/80. A ratio of 0.1/99.9 or more is preferred since the effects generated by the effective components in the oil component are likely to be exhibited sufficiently. On the other hand, a ratio of 50/50 or less is preferable since it is easy to obtain an emulsion having such a particle diameter that transparency is not impaired. The components contained in the oil phase and the water phase in the production method are the same as the constituents of the powder composition described above according to the invention, and preferred examples and preferred amount are also the same; the preferred combinations given in the explanation of the powder composition are more preferred also in the production method.

The powder composition according to the invention may contain other components that are generally used, in addition to the above-described components. Examples of such other component include radical scavengers and excipients.

A radical scavenger is an additive that suppresses generation of radicals, and further has a role of rapidly trapping generated radicals, thereby stopping a chain reaction (Source: Oil Chemistry Handbook, 4th edition, Japan Oil Chemists' Association, 2001).

Known methods for directly confirming the function as a radical scavenger include mixing a subject compound with a reagent and measuring the process of radical trap by the compound with a spectrophotomer or by ESR (electron spin resonance). In those methods, DPPH (1,1-diphenyl-2-picrylhydrazyl) or a garbinoxyl radical is used as the reagent.

Under the following experimental conditions, the time required to increase the peroxide value (POV) of an oil to 60 meq/kg through an auto-oxidation reaction of oil is measured. In the invention, a compound is defined as a "radial scavenger" if the required time is at least 2 times the time required for a blank. The peroxide value (POV) of oil is measured with a conventional method.

<Conditions>
Oil: Olive oil
Amount of specimen added: 0.1% by mass based on mass of oil
Test method: Sample is heated to 190° C., POV values are measured by a conventional method with the passage of time, and the time required to reach a POV of 60 meq/kg is determined.

The radical scavenger in the invention is preferably such a scavenger that the time required to reach POV of 60 meq/kg is at least 5 times the time required for a blank, from the standpoint of stability of an emulsion against oxidation.

Compounds that can be used as the radical scavenger in the invention include compounds functioning as a radical scavenger selected from various antioxidants described in "Theory and Fact of Antioxidant" (Kajimoto, San Shobo, 1984) and "Antioxidant Handbook" (Saruwatari, Nishino and Tabata, Taiseisha, 1976); specific examples thereof include compounds having a phenolic OH, amine compounds such as phenylenediamine, and oil-solubilized derivatives of ascorbic acid and erythorbic acid.

Preferred examples of the radical scavenger (antioxidant) include at least two compounds selected from (I) a group of compounds consisting of ascorbic acid, salts of ascorbic acid, erythorbic acid, salts of erythorbic acid, ascorbic acid derivatives, salts of ascorbic acid derivatives, erythorbic acid derivatives and salts of erythorbic acid derivatives, and (II) a group of compounds consisting of polyphenols.

The content of radical scavenger in the emulsion composition is generally from 0.001 to 5.0% by mass, preferably from 0.01 to 3.0% by mass, and more preferably from 0-1 to 2.0% by mass.

(I) Ascorbic Acid, Erythorbic Acid and Salts thereof

Examples of ascorbic acid, ascorbic acid derivatives and salts thereof include L-ascorbic acid, sodium L-ascorbate, potassium L-ascorbate, calcium L-ascorbate, L-ascorbic phosphate, L-ascorbic phosphate magnesium salt, L-ascorbic sulfate, L-ascorbic sulfate disodium salt, L-ascorbic stearate, L-ascorbic 2-glucoside, L-ascorbic palmitate and L-ascobyl tetraisopalmitate. Of those, L-ascorbic acid, sodium L-ascorbate, L-ascorbic stearate, L-ascorbic 2-glucoside, L-ascorbic palmitate, L-ascorbic phosphate magnesium salt, L-ascorbic sulfate disodium salt and L-ascorbyl tetraisopalmitate are particularly preferred.

Examples of erythorbic acid, erythorbic acid derivatives and salts thereof include erythorbic acid, sodium erythorbate, potassium erythorbate, calcium erythorbate, erythorbic phosphate, erythorbic sulfate, erythorbic palmitate and erythorbic tetraisopalmitate. Of those, erythorbic acid and sodium erythorbate are particularly preferred.

A radical scavenger usable in the invention belonging to the group (I) of compounds may be appropriately selected from commercially available products. Examples thereof L-ascorbic acid (Takeda Pharmaceutical Company Limited, Fuso Chemical Co., Ltd., BASF Japan, Daiichi Pharmaceutical Co., Ltd., and the like), sodium L-ascorbate (Takeda Pharmaceutical Company Limited, Fuso Chemical Co., Ltd., BASF Japan, Daiichi Pharmaceutical Co., Ltd., and the like), L-ascorbic acid 2-glucoside (trade name: AA-2G, Hayashibara Biochemical Labs., Inc.), L-ascorbic magnesium phosphate (trade name: Ascorbic Acid PM "SDK", Showa Denko K.K.); trade name NIKKOL VC-PMG (Nikko Chemicals Co., Ltd.); trade name: C MATE (Takeda Pharmaceutical Company Limited)), and ascorbyl palmitate (DSM Nutrition Japan, Kongo Yakuhin Co., Ltd., Merck Ltd., and the like).

Group (II) of Compounds Consisting of Polyphenols

Examples of the group of compounds consisting of polyphenols include flavonoids (catechin, anthocyanin, flavone, isoflavone, flavane, flavanone and rutin), phenolic acids (chlorogenic acid, ellagic acid, gallic acid and propyl gallate), lignans, curcumins and coumarins. Those compounds are contained, in a significant amount, in the following naturally-derived extracts, and therefore can be used in the state of an extract.

Examples of naturally-derived extracts include a licorice extract, a cucumber extract, a *Millettia reticulata* extract, a gentian extract, a *Geranium thunbergii* extract, a cholesterol and its derivatives, a hawthorn extract, a peony extract, a gingko extract, a Baikai skullcup extract, a carrot extract, a rugosa rose (Maikai) extract, a Chamaecrista nomame extract, a Tormentil extract, a parsley extract, a peony extract, a Japanese quince extract, a Melissa extract, an alnus firma fruit extract, a strawberry geranium extract, a rosemary extract, a lettuce extract, a tea extract (oolong tea, black tea, green tea and the like), a microbial fermentation metabolic product and a *Momordica grosvenori* Swingle extract. Of those polyphenols, particularly preferred are catechin, a rosemary extract, glucosyl rutin, ellagic acid and gallic acid.

Radical scavengers belonging to the group (II) of compounds usable in the invention may be appropriately selected from commercially available products. Examples thereof include ellagic acid (Wako Pure Chemical Industries, Ltd., and the like), rosemary extracts (trade name: RM-21A, RM-21E, Mitsubishi-Kagaku Foods Corporation, and the like), catechin (trade name: SANKATOL W-5, No. 1, Taiyo Kagaku Co., Ltd., and the like), sodium gallate (trade name: SANKATOL, Taiyo Kagaku Co., Ltd., and the like), and rutins, glurcosylrutins and enzymatically decomposed rutins (trade name: Rutin K-2, P-10, Kiriya Chemical Co., Ltd.; trade name: αG Rutin, Hayashibara Biochemical Labs., Inc.; and the like).

According to need, the powder composition according to the invention may further contain an excipient so as to impart tableting suitability or granulation suitability.

The excipient may be a generally-used water-soluble material, and examples thereof include monosaccharides and polysaccharides such as glucose, fructose, lactose, malt sugar, sucrose, dextrin, maltodextrin, cyclodextrin, maltose and trehalose; sugar alcohols such as sorbitol, mannitol, maltitol, lactose, maltotriitol and xylitol; inorganic salts such as sodium chloride and sodium sulfate; polysaccharide thickeners such as gum arabic, guar gum, pectin, pullulan and sodium alginate; cellulose derivatives such as hydroxyethyl cellulose and hydroxypropyl cellulose; starch derivatives obtained by subjecting starch to esterification, etherification or terminal reduction treatment; processed starches, gelatin hydrolysates, agars and polyvinyl alcohols. Of those, monosaccharides, polysaccharides, sugar alcohols and inorganic salts are preferred from the point of solubility, gum arabic, dextrin, sugar alcohols and inorganic salts are more preferred from the standpoint of humidity absorption property and particle formability, and gum arabic and dextrin are particularly preferred. Only a single excipient may be used, or two or more excipients may be used in combination.

The amount of excipient to be used is preferably from 0 to 40% by mass, more preferably from 0 to 30% by mass, based on the mass of the water-soluble encapsulating agent (A) or (B) according to the first or second embodiment, from the standpoint of shape retention and solubility.

According to need, one or more other additives may appropriately be added to the powder composition according to the invention. The powder composition may contain a polyhydric alcohol that is liquid at ordinary temperature. In this case, the content of the polyhydric alcohol is preferably 10% by mass or less, more preferably 5% by mass or less, based on the mass of the water-soluble encapsulating agent from the standpoint of ease of powderization. The polyhydric alcohol used herein means a dihydric or higher-hydric alcohol. Examples thereof include glycerin, diglycerin, triglycerin, polyglycerin, 3-methyl-1,3-butanediol, 1,3-butylene glycol, isoprene glycol, polyethylene glycol, 1,2-pentanediol, 1,2-hexanediol, propylene glycol, dipropylene glycol, polypropylene glycol, ethylene glycol, diethylene glycol, pentaerythritol, and neopentyl glycol. Only a single polyhydric alcohol may be used, or a mixture of plural polyhydric alcohols may be used.

The powder composition according to the first embodiment may be obtained by preparing an emulsion composition containing the components described above, and drying the emulsion composition.

Specifically, a method for producing a powder composition according to the first embodiment may include (i) emulsifying at least one functional oil component in an aqueous medium in the presence of at least one emulsifier selected from sucrose fatty acid esters, polyglycerin fatty acid esters and phospholipids to obtain an emulsion composition (emulsification step), (ii) adding to the aqueous medium and/or the emulsion composition at least one water-soluble encapsulating agent selected from saccharides containing at least two sugar units including a fructose unit, and (iii) drying the emulsion composition containing the water-soluble encapsulating agent (drying step).

In the emulsification step in the production method, an oil-in-water emulsion composition in which oil droplets containing, among the various components, the functional oil component are finely dispersed in water is obtained. Regarding addition of the water-soluble encapsulating agent (A), the water-soluble encapsulating agent (A) may be added to the water phase before the emulsification step, or may be added after the emulsification. It is preferred to add the water-soluble encapsulating agent (A) before the emulsification from the standpoint of encapsulation of oil droplets. Any generally-known emulsification method may be used, such as a natural emulsification method, an interfacial chemical emulsification method, an electrical emulsification method, a capillary emulsification method, a mechanical emulsification method and an ultrasonic emulsification method.

The powder composition according to the second embodiment may be obtained by preparing an emulsion composition containing the components described above, and drying the emulsion composition.

A method for producing a powder composition containing a functional oil component according to the second embodiment may include (i) emulsifying at least one functional oil component in an aqueous medium, in the presence of at least one emulsifying agent selected from sucrose fatty acid esters, polyglycerin fatty acid esters and phospholipids to obtain an emulsion composition (emulsification step), (ii) adding to the aqueous medium and/or the emulsion composition at least one water-soluble encapsulating agent (B) selected from saccharides containing at least one galactose unit and one fructose unit (addition step) and (iii) drying the emulsion composition containing the water-soluble encapsulating agent (B) (drying step).

In the emulsification step in the production method, an oil-in-water emulsion composition in which oil droplets containing, among the various components, the functional oil component are finely dispersed in water is obtained. The addition of the water-soluble encapsulating agent (B) may be conducted either before or after the emulsification. For example, the water-soluble encapsulating agent (B) may be added to the water phase—i.e., an aqueous medium such as water—before the emulsification step, or may be added to the obtained emulsion composition after the emulsification. It is also possible to add a part of the water-soluble encapsulating agent (B) before and after the emulsification. The addition step of the water-soluble encapsulating agent (B) is preferably conducted before the emulsification from the viewpoint of encapsulating the oil droplets effectively. Any generally-known emulsification method may be used, such as a natural emulsification method, an interfacial chemical emulsification method, an electrical emulsification method, a capillary emulsification method, a mechanical emulsification method and an ultrasonic emulsification method.

Explanations common to both embodiments are resumed. Interfacial chemical emulsification methods such as a PIT emulsification method and a gel emulsification method are known as effective methods for forming fine particle emulsion. These method are advantageous in that the energy consumption is small, and are therefore suitable to fine emulsification of a material that is easily deteriorated by heat.

A generally-used emulsification method is a method of using mechanical force, that is, a method of applying strong shear force from outside so as to split oil droplets. The most common form of the mechanical force is a high speed, high shear force stirring machine, which may be selected from commercially available devices called homomixers, disper mixers and ultramixers.

Other useful mechanical emulsification apparatuses for reducing the particle size include various commercially available high-pressure homogenizers. The high-pressure homogenizers can apply large shearing force as compared with a stirring type apparatuses, and reduction in the particle size is possible even when the amount of emulsifier is relatively small.

The high-pressure homogenizers are largely classified into chamber high-pressure homogenizers having a fixed throttle part, and homogeneous-valve high-pressure homogenizers that allow control of throttle opening.

Examples of chamber high-pressure homogenizers include MICROFLUIDIZER (manufactured by Microfluidics), NANOMIZER (manufactured by Yoshida Kikai Co., Ltd.), and ALTIMIZER (manufactured by Sugino Machine Limited).

Examples of homogeneous-valve high-pressure homogenizers include Gaulin homogenizer (manufactured by APV), Ranie homogenizer (manufactured by Ranie), high-pressure homogenizer (manufactured by Niro Soavi), homogenizer (manufactured by Sanwa Machine Co., Ltd.), high-pressure homogenizer (manufactured by Izumi Food Machinery Co., Ltd.) and ultrahigh-pressure homogenizer (manufactured by IKA).

Ultrasonic homogenizers are emulsification apparatuses having a simple structure, which are dispersion apparatuses with relatively high energy efficiency. Examples of a high-power ultrasonic homogenizer that can be produced include Ultrasonic homogenizer US-600, Ultrasonic homogenizer US-1200T, Ultrasonic homogenizer RUS-1200T and Ultrasonic homogenizer MUS-1200T (manufactured by Nissei Corporation), and Ultrasonic processor UIP2000, Ultrasonic processor UIP-4000, Ultrasonic processor UIP-8000 and Ultrasonic processor UIP-16000 (manufactured by Hielscher). Those high-power ultrasonic irradiation apparatuses are used at a frequency of 25 kHz or less, preferably from 15 to 20 kHz.

Other known emulsification means include methods of using a static mixer, a microchannel, a micromixer, a membrane emulsification apparatus or the like, each of which requires only a low energy and does not have a stirring portion connected to the outside. These methods are also useful.

The temperature condition at emulsification dispersion in the invention is not particularly limited. The temperature is preferably from 10 to 100° C. from the standpoint of stability of the functional oil component. A preferred temperature range may be appropriately selected in accordance with the melting point of the functional oil component to be used, and the like.

When a high-pressure homogenizer is used in the invention, the processing pressure is preferably 50 MPa or more, more preferably from 50 to 250 MPa, and further preferably from 100 to 250 MPa.

It is preferred from the standpoint of maintaining the particle diameter of dispersed particles that an emulsion liquid, which is a emulsified and dispersed composition, is cooled through a cooler within 30 seconds, preferably within 3 seconds, from passing through the chamber.

The oil-in-water emulsion composition obtained by emulsification is then dried and powdered in a powderization step.

In the oil-in-water emulsion composition according to the first embodiment, the functional oil component is encapsulated with the water-soluble encapsulating agent (A). Therefore, a dried powder that is easy to disperse in water can be obtained by drying the emulsion. As a result, a functional powder in which the functional oil component maintains its fine oil droplet state is can be formed.

In the powder composition obtained by the production method of a functional powder in the first embodiment, a large proportion of water in the emulsion has been removed. Therefore, it is possible to prevent oil droplets from getting bigger due to coalescence, prevent deterioration of the functional oil component due to, for example, hydrolysis, and prevent putrefaction and molds during storage. Additionally, since the weight can be reduced by removing water in the emulsion to obtain a functional powder, the transportation costs can be greatly decreased.

In the oil-in-water emulsion composition according to the second embodiment, the use of the galactose/fructose-containing saccharide as a water-soluble encapsulating agent (B) enables control of the emulsion composition to a satisfactory dry state during the drying step, and prevention of adhesion of the emulsion composition to the drying apparatus, surrounding walls, and the like. As a result, the loss in the drying step can be reduced to improve the yield.

Further, since the functional oil component is encapsulated with the water-soluble encapsulating agent (B) described above, a dry powder that is easy to disperse in water can be obtained by drying the emulsion. As a result, a functional powder in which the functional oil component maintains its fine oil droplet state is can be formed. Moreover, in the powder composition obtained by the production method of a functional powder in the second embodiment, a large proportion of water in the emulsion has been removed. Therefore, it is possible to prevent oil droplets from getting bigger due to coalescence, and excellent transparency after redissolution can be achieved.

In the powder composition according to the second aspect, a satisfactory dry state of the emulsion composition can be realized, whereby the yield of the powder composition after the drying step can be made high. Such a high yield may be, though depending on the drying means and the composition of the emulsion composition, for example 80% by mass or more, preferably 85% by mass or more, in terms of the ratio of the mass of the powder composition after drying to the mass of the solid content of the emulsion composition before drying.

Descriptions common to the first and second embodiments are resumed. Usable drying means include conventional drying means, and examples thereof include natural drying, heat drying, hot air drying, high frequency drying, ultrasonic drying, reduced pressure drying, vacuum drying, freeze drying and spray drying. Only a single means may be used, or a combination of two or more drying means may be used.

In the invention, since there are many cases where functional materials that are relatively weak to heat are contained, reduced pressure drying, vacuum drying, freeze drying and spray drying are preferred. A method of vacuum (reduced pressure) drying while maintaining a temperature that is no higher than 0° C. but no lower than the freezing temperature, which is one way to vacuum dry, is also preferred.

Where vacuum drying or reduced pressure drying, it is preferred that drying is conducted by repeating concentration with gradually increased vacuum degree, in order to avoid scattering of an emulsion due to bumping.

The method for drying the emulsion according to the invention is preferably freeze drying, in which water is removed through sublimation of ice from a material in a frozen state. In this freeze drying method, the drying process generally proceeds at 0° C. or lower, more generally from about −20° C. to −50° C. Therefore, heat denaturation of a material does not occur, and there is a big advantage in that taste, color, nutrition value, shape, texture and the like are likely to be restored, in the course of water recovery, to the same state as those before drying.

Examples of the commercially available freeze dryers include, but are not limited to, Freeze Dryer VD-800F (Tietech Co.), Flexdry MP (FTS Systems), Dura Top/Dura Stop (FTS Systems), Takara vacuum freeze dryer Model A (Takara ATM), Desk freeze dryer FD-1000 (Tokyo Rikakikai Co., Ltd.), Vacuum freeze dryer FD-550 (Tokyo Rikakikai Co., Ltd.) and Vacuum freeze dryer (Takara Seisakusho).

In the invention, spray drying method is particularly preferred as drying means from the standpoint of securing both of production efficiency and quality. The spray drying is a kind of convection hot air dryer. A liquid emulsion is sprayed in the form of fine particles having a size of several hundred μm or less in hot air, allowed to fall down in a tower while dried, and recovered as a solid powder. Although the material is temporarily exposed to hot air, the temperature thereof does not elevate so much because of very short exposure time and evaporation latent heat of water. Therefore, similar to the freeze drying, heat denaturation of the material hardly occurs, and change caused by water recovery is small. In the case of a material that is very weak to heat, it is possible to supply cold air in place of hot air, which is preferable in the point that milder drying can be realized though drying ability drops.

Examples of conventionally available spray dryers include, but are not limited to, Spray dryer SD-1000 (Tokyo Rikakiki Co., Ltd.), Spray dryer L-8i (Ogawara Kakoki Co., Ltd.), Closed spray dryer CL-12 (Ogawara Kakoki Co., Ltd.), Spray dryer ADL310 (Yamato Scientific Co., Ltd.), Minispray dryer B-290 (Buchi), PJ-MiniMax (Powering Japan), and PHAR-MASD (Niro).

Furthermore, it is preferred to form granulated powder with excellent handling properties simultaneously with drying by using an apparatus that can simultaneously conduct drying and granulation, such as Fluidized bed granulation dryer MP-01 (Powrex Corporation) and Fluidized bed built-in spray dryer FSD (Niro).

The powder according to the invention has water recovery property, that is, the ability to restore the pre-drying emulsion state when dissolved in water again.

When drinks, functional foods, cosmetics and the like are produced using this functional powder, drinks, functional foods, cosmetics and the like can easily be produced.

Furthermore, by using this functional powder, the function can be exhibited without impairing the function of the functional component, and appearance such as transparency of a redispersed product and stability during storage are also made satisfactory.

If the particle diameter of the functional powder according to the invention that has recovered water is greatly increased relative to the particle diameter before drying, it is considered that there is a high possibility that oil droplets coalesced in the course of drying.

The transparency of the powder composition according to the invention at the time of redissolution can be evaluated based on the particle diameter of oil droplets at the time of redissolution. In the evaluation, when a 1% by mass aqueous solution is formed (water recovery), the particle diameter of the oil droplets is preferably from 10 to 500 nm from the standpoints of transparency and absorption properties, and is particularly preferably from 10 to 200 nm from the standpoints of good transparency, dispersion stability, and the above-described various storage stabilities.

The particle size of the oil-in-water emulsion composition according to the invention can be measured with a commercially available particle size distribution measuring device. Known methods for particle size distribution measurement include optical microscopy, confocal laser microscopy, electron microscopy, atomic force microscopy, static light scattering method, laser diffraction method, dynamic light scattering method, centrifugal precipitation method, electric pulse measurement method, chromatography method, and ultrasonic attenuation method, and devices corresponding to the respective principles are commercially available.

In consideration of the particle size range in the invention and the case of measurement, a dynamic light scattering method is preferred in the emulsion particle size measurement in the invention. Commercially available measurement devices using dynamic light scattering include NANOTRAC UPA (Nikkiso Co., Ltd.), dynamic light scattering particle size distribution measuring device LB-550 (Horiba, Ltd.) and fiber-optics particle size analyzer FPAR-1000 (Otsuka Electronics Co., Ltd.).

The particle size of the emulsion composition can be adjusted by controlling the components of the emulsion composition, or by controlling other factors such as the stirring conditions (shearing force, temperature and pressure) in the production method of the emulsion composition and the oil phase/water phase ratio.

The particle diameter in the invention refers to a value measured at 25° C. with a dynamic light scattering particle diameter distribution measuring instrument.

As described above, the powder composition according to the first embodiment provides excellent transparency and dispersion stability, as well as excellent storage stability of components contained, storage stability of particle diameter and emulsion storage stability. Therefore, it is preferred to apply the powder composition to food compositions, cosmetic compositions and pharmaceutical compositions.

In other words, food compositions, cosmetic compositions and pharmaceutical compositions according to the first embodiment each contain the powder composition according to the first embodiment.

The powder composition according to the second embodiment provides reduction in the loss during production, excellent transparency and dispersion stability, as well as excellent storage stability of components contained, storage stability of particle diameter and emulsion storage stability. Therefore, it is preferred to apply the powder composition to food compositions, cosmetic compositions and pharmaceutical compositions.

In other words, food compositions, cosmetic compositions and pharmaceutical compositions according to the second embodiment each contain the powder composition according to the first embodiment.

Common explanations to the first and second embodiments are resumed. Examples of the food include, but are not limited to, drinks and frozen desserts, and examples of the cosmetic include skin cosmetics (skin lotion, serum, milky lotion, cream and the like), lipsticks, sunscreen cosmetics and makeup cosmetics, and examples of the pharmaceuticals include, but are not limited to, nutrient-supplement drinks and revitalizers.

The food compositions, cosmetic compositions and pharmaceutical compositions according to the invention can be obtained by, for example, mixing a powder composition according to the invention and optional components that can be added for achieving the desired purpose by a conventional method.

The powder composition in the powder state may be mixed with other components, or a solution obtained by redissolving the powder composition may be added to other components, depending on the type of the desired product compositions.

The addition amount of the powder composition according to the invention, which may be used in foods, cosmetics, medicines and the like, varies depending on the kind and purpose of the product, and cannot be uniquely defined. However, the addition amount of the powder composition with respect to the product may be from 0.01 to 10% by mass, and preferably from 0.05 to 5% by mass.

When the addition amount is 0.01% by mass or more, desired effects may be obtained, and when the amount is 10% by mass or less, appropriate effects are likely to be achieved effectively.

The powder composition according to the invention can be stored in the powder state over a long period of time. In particular, when the powder composition is redissolved and used in aqueous products such as drinks (in the case of foods), skin lotions, serums, milky lotions, cream packs and masks, packs, shampoo cosmetics, fragrance cosmetics, liquid body cleaning preparations, UV care cosmetics, deodorants, and oral health cosmetics (in the case of cosmetics), products having transparent feeling can be obtained. Additionally, disadvantageous phenomena such as segregation, precipitation and choker ring of insoluble substance under severe conditions such as long-term storage or sterilization treatment can be suppressed from being generated.

Disclosures of Japanese Patent Application Nos. 2007-027287 and 2007-174556 are incorporated herein by reference.

EXAMPLES

The present invention is described more specifically by reference to the following Examples. In the following description, "part" and "%" are based on mass ("part by mass" and "% by mass", unless otherwise indicated.

Example 1

(Preparation of Powder Sample A-1)
(Preparation of Emulsion)

The following components were dissolved at 70° C. for 1 hour, and homogenized using Ultrasonic homogenizer U600 Model, manufactured by Nissei Corporation, for 1 minute to obtain a water phase composition A-1.

| | |
|---|---|
| Sucrose laurate ester: | 5.2 g |
| Decaglyceryl monolaurate: | 5.2 g |
| Lecithin (derived from soybean): | 1.9 g |
| Inulin (derived from dahlia root): | 34.3 g |
| Pure water: | 246.8 g |

The following components were dissolved at 70° C. for 1 hour to obtain an oil phase composition A-1.

| | |
|---|---|
| *Haematococcus alga* extract (Astaxanthins content: 20% by mass): | 5.2 g |
| Mix tocopherol: | 1.4 g |

The sucrose laurate ester used above was RYOTO sugar ester L-1695 manufactured by Mitsubishi-Kagaku Foods Corporation, and the decaglyceryl monolaurate used above was NIKKOL Decaglyn 1-L manufactured by Nikko Chemicals Co., Ltd. The *Haematococcus alga* extract used above was ASTOTS-S manufactured by Takeda Shiki Co., Ltd. The mix tocopherol used above was Riken E Oil 800 manufactured by Riken Vitamin Co., Ltd. The lecithin (derived from soybean) used above was LECION P manufactured by Riken Vitamin Co., Ltd. The inulin used above was a product of Wako Pure Chemical Industries, Ltd. (Catalogue No. 069-00322).

Immediately after the water phase A-1 and the oil phase A-1 obtained above were mixed, the mixture was emulsified with the above-described ultrasonic homogenizer for 20 minutes. The ultrasonic irradiation was conducted while the liquid was cooled so as to maintain the liquid temperature at 60° C. and was stirred with a magnetic stirrer so as to homogenize the liquid. The resultant emulsion was collected, and was immediately cooled to room temperature, whereby an astaxanthin-containing oil-in-water emulsion A-1 was obtained.

(Spray Drying)

The emulsion A-1 obtained above was spray dried with a Spray dryer ADL 310 Model manufactured by Yamato Scientific Co., Ltd. under the conditions of a spray pressure of 0.15 MPa, an outlet temperature of 80° C. and a processing amount of 7 ml/min, thereby obtaining a dry powder sample A-1. The mass of the dry powder that could be collected by drying 100 g of the emulsion was weighed, and the yield relative to the theoretical amount was calculated.

(Preparation of Powder Sample B-1)

Sample B-1 was prepared in the same manner as the preparation of sample A-1, except that BENEO HP (derived from chicory root, average degree of polymerization of fructose: 23) manufactured by Orafti was used in place of the inulin manufactured by Wako Pure Chemical Industries, Ltd.

(Preparation of Powder Sample C-1)

Sample C-1 was prepared in the same manner as the preparation of sample A-1, except that BENEO ST (oligofructose derived from chicory root, average degree of polymerization of fructose: 10) manufactured by Orafti was used in place of the inulin manufactured by Wako Pure Chemical Industries, Ltd.

(Preparation of Powder Sample D-1)

Sample D-1 was prepared in the same manner as the preparation of sample A-1, except that Fuji FF (derived from sugar, average degree of polymerization of fructose: 16) manufactured by Fuji Nippon Seito Corporation was used in place of the inulin manufactured by Wako Pure Chemical Industries, Ltd.

(Preparation of Powder Sample E-1)

Sample E-1 was prepared in the same manner as the preparation of sample A-1, except that GF2 (kestose, derived from sugar, average degree of polymerization of fructose: 2) manufactured by Meiji Seika Kaisha, Ltd. was used in place of the inulin manufactured by Wako Pure Chemical Industries, Ltd.

(Preparation of Powder Sample F-1)

Sample F-1 was prepared in the same manner as the preparation of sample A-1, except that oligotose (maltotriose) manufactured by Mitsubishi-Kagaku Foods Corporation was used in place of the inulin manufactured by Wako Pure Chemical Industries, Ltd.

(Preparation of Powder Sample G-1)

Sample G-1 was prepared in the same manner as the preparation of sample A-1, except that sucrose (degree of polymerization of fructose: 1) manufactured by Wako Pure Chemical Industries, Ltd. was used in place of the inulin manufactured by Wako Pure Chemical Industries, Ltd.

(Preparation of Powder Sample H-1)

Sample H-1 was prepared in the same manner as the preparation of sample A-1, except that instant gum AB (arabia gum) manufactured by Colloid Nature was used in place of the inulin manufactured by Wako Pure Chemical Industries, Ltd.

(Preparation of Powder Sample I-1)

Sample I-1 was prepared in the same manner as the preparation of sample D-1, except that the addition amount of Fuji FF was changed to 17.2 g, and the amount of water in the water phase at the time of emulsification was changed to 263.9 g.

(Preparation of Powder Sample J-1)

Sample J-1 was prepared in the same manner as the preparation of sample D-1, except that sucrose stearate ester was used in place of sucrose laurate ester. The sucrose stearate ester used above was RYOTO sugar ester S-1670 manufactured by Mitsubishi-Kagaku Foods Corporation.

(Preparation of Powder Sample K-1)

Sample K-1 was prepared in the same manner as the preparation of sample D-1, except that decaglyceryl monooleate was used in place of decaglyceryl monolaurate. The decaglyceryl monooleate used above was NIKKOL Decaglyn 1-O manufactured by Nikko Chemicals Co., Ltd.

Evaluation (Redissolved Particle Diameter Measurement)

99.0 g of pure water was added to 1.00 g of each of astaxanthin-containing powders (A-1 to K-1) obtained, followed by stirring with a magnetic stirrer for 5 minutes. The particle diameter of each of the aqueous emulsions obtained was measured with a dynamic light scattering particle diameter analyzer FPAR-1000 (manufactured by Otsuka Electronics Co., Ltd.) at 25° C. The value of an average particle diameter was shown by a median diameter.

(Stability of Powder Over Time)

Each of the powders A-1 to K-1 obtained above was placed in a glass bottle with a cap, and the glass bottle was stored in a thermostatic bath maintained at 50° C. for four weeks.

Colorant Concentration Measurement

In order to evaluate the colorant concentrations of the solutions obtained by redissolving in water each of powders A-1 to K-1 before and after the four-week storage, a spectral absorption measurement was conducted with a spectrophotometer (ND-1000; manufactured by Nanoprop Technologies). The absorbance at 479 nm before the storage was represented by "Ab0", and the absorbance at 479 nm after the storage was represented by "Ab1". A colorant residual ratio was obtained by the following equation. When storage stability is poor, the colorant residual ratio is low.

Colorant residual ratio (%)=$Ab1/Ab0 \times 100$

Average Particle Diameter

The average particle diameters of the particles in the solutions obtained by redissolving in water each of powders A-1 to K-1 before and after the four-week storage were measured at 25° C. according to the particle diameter measurement method described above.

The results are shown in Tables 1 and 2.

The results indicate that the powder samples according to the invention showed small average particle diameters when redissolved in water, the liquids obtained by the redissolution were transparent, and the change in their particle diameters was small even after the forced storage at 50° C. It was also found that, in the samples according to the invention, the reduction in the color density caused by deterioration of astaxanthin during the forced storage at 50° C. is suppressed.

Therefore, according to the invention, a powder composition is provided which enables protection of fine oil droplets during dry storage and provides transparency and storage stability even after redissolution.

TABLE 1

|  | Matrix material |  | Degree of polymerization of fructose | Matrix material/ oil component ratio | Lecithin | Polyglycerin fatty acid ester | Sucrose fatty acid ester |
|---|---|---|---|---|---|---|---|
| A-1 | Invention | Inulin | — | 5.2 | Included | Included | Included |
| B-1 | Invention | Inulin | 23 | 5.2 | Included | Included | Included |
| C-1 | Invention | Inulin | 10 | 5.2 | Included | Included | Included |
| D-1 | Invention | Inulin | 16 | 5.2 | Included | Included | Included |
| E-1 | Invention | Kestose | 2 | 5.2 | Included | Included | Included |
| F-1 | Comparative Example | Maltotriose | — | 5.2 | Included | Included | Included |
| G-1 | Comparative Example | Sucrose | 1 | 5.2 | Included | Included | Included |
| H-1 | Comparative Example | Gum arabic | — | 5.2 | Included | Included | Included |
| I-1 | Invention | Inulin | 16 | 2.6 | Included | Included | Included |
| J-1 | Invention | Inulin | 16 | 5.2 | Included | Included | Not Included |
| K-1 | Invention | Inulin | 16 | 5.2 | Included | Not Included | Included |

TABLE 2

|  |  | Average particle diameter before storage (nm) | Average particle diameter after four-week storage at 50° C. (nm) | Colorant residual ratio after four-week storage at 50° C. (%) |
|---|---|---|---|---|
| A-1 | Invention | 145 | 146 | 95 |
| B-1 | Invention | 139 | 142 | 93 |
| C-1 | Invention | 106 | 105 | 90 |
| D-1 | Invention | 101 | 103 | 95 |
| E-1 | Invention | 103 | 110 | 89 |
| F-1 | Comparative Example | 156 | 189 | 73 |
| G-1 | Comparative Example | 256 | 348 | 66 |
| H-1 | Comparative Example | 230 | 258 | 85 |
| I-1 | Invention | 112 | 120 | 88 |
| J-1 | Invention | 98 | 106 | 90 |
| K-1 | Invention | 116 | 115 | 97 |

Example 2

(Preparation of Emulsion)

The following components were dissolved at 70° C. for 1 hour, and homogenized using Ultrasonic homogenizer U600 Model manufactured by Nissei Corporation for 1 minute to obtain a water phase composition A-2.

| Sucrose laurate ester: | 5.2 g |
|---|---|
| Decaglyceryl monolaurate: | 5.2 g |
| Lecithin (derived from soybean): | 1.9 g |
| Raffinose (derived from beet): | 34.3 g |
| Pure water: | 246.8 g |

The following components were dissolved at 70° C. for 1 hour to obtain an oil phase composition A-2.

| | |
|---|---|
| *Haematococcus alga* extract (Astaxanthins content: 20% by mass): | 5.2 g |
| Mix tocopherol: | 1.4 g |

The sucrose laurate ester used above was RYOTO sugar ester L-1695 manufactured by Mitsubishi-Kagaku Foods Corporation, and the decaglyceryl monolaurate used above was NIKKOL Decaglyn 1-L manufactured by Nikko Chemicals Co., Ltd. The *Haematococcus alga* extract used above was ASTOTS-S manufactured by Takeda Shiki Co., Ltd. The mix tocopherol used above was Riken E Oil 800 manufactured by Riken Vitamin Co., Ltd. The lecithin (derived from soybean) used above was LECION P manufactured by Riken Vitamin Co., Ltd. The raffinose used above was a product of Nippon Beet Sugar Manufacturing Co., Ltd.

Immediately after the water phase A-2 and the oil phase A-2 obtained above were mixed, the mixture was emulsified with the above-described ultrasonic homogenizer for 20 minutes. The ultrasonic irradiation was conducted while the liquid was cooled so as to maintain the liquid temperature at 60° C. and was stirred with a magnetic stirrer so as to homogenize the liquid. The resultant emulsion was collected, and was immediately cooled to room temperature, whereby an astaxanthin-containing oil-in-water emulsion A-2 was obtained.

(Spray Drying)

The emulsion A-2 obtained above was spray dried with a Spray dryer ADL 310 Model manufactured by Yamato Scientific Co., Ltd. under the conditions of a spray pressure of 0.15 MPa, an outlet temperature of 80° C. and a processing amount of 7 ml/min, thereby obtaining a dry powder sample A-2. The mass of the dry powder that could be collected by drying 100 g of the emulsion was weighed, and the yield relative to the theoretical amount was calculated.

(Preparation of Powder Sample B-2)

Sample B-2 was prepared in the same manner as the preparation of sample A-2, except that stachyose (SFS oligosaccharide manufactured by Garyu Honpo, Westone Co., Ltd.) was used in place of raffinose.

(Preparation of Powder Sample C-2)

Sample C-2 was prepared in the same manner as the preparation of sample A-2, except that maltotriose (OLIGOTOSE manufactured by Mitsubishi-Kagaku Foods Corporation) is used in place of raffinose.

(Preparation of Powder Sample D-2)

Sample D-2 was prepared in the same manner as the preparation of sample A-2, except that kestose (GF2 manufactured by Meiji Seika Kaisha, Ltd.) was used in place of raffinose.

(Preparation of Powder Sample E-2)

Sample E-2 was prepared in the same manner as the preparation of sample A-2, except that palatinose manufactured by Mitsui Sugar Co., Ltd. was used in place of raffinose.

(Preparation of Powder Sample F-2)

Sample F-2 was prepared in the same manner as the preparation of sample A-2, except that lactose (special grade: manufactured by Wako Pure Chemical Industries, Ltd.) was used in place of raffinose.

(Preparation of Powder Sample G-2)

Sample G-2 was prepared in the same manner as the preparation of sample A-2, except that gum arabic (instant gum AB manufactured by Colloid Nature) was used in place of raffinose.

(Preparation of Powder Sample H-2)

Sample H-2 was prepared in the same manner as the preparation of sample A-2, except that a modified starch (PINEDEX #1 manufactured by Matsutani Chemical Industry Co., Ltd.) was used in place of raffinose.

(Preparation of Powder Sample I-2)

Sample I-2 was prepared in the same manner as the preparation of sample A-2, except that the addition amount of raffinose was changed to 17.2 g, and the amount of water in the water phase at the time of emulsification was changed to 263.9 g.

(Preparation of Powder Sample J-2)

Sample J-2 was prepared in the same manner as the preparation of sample A-2, except that sucrose stearate ester was used in place of sucrose laurate ester. The sucrose stearate ester used above was RYOTO sugar ester S-1670 manufactured by Mitsubishi-Kagaku Foods Corporation.

(Preparation of Powder Sample K-2)

Sample K-2 was prepared in the same manner as the preparation of sample A-2, except that decaglyceryl monooleate was used in place of decaglyceryl monolaurate. The decaglyceryl monooleate used above was NIKKOL Decaglyn 1-0 manufactured by Nikko Chemicals Co., Ltd.

Evaluation (Redissolved Particle Diameter Measurement)

99.0 g of pure water was added to 1.00 g of each of astaxanthin-containing powders (A-2 to K-2) obtained, followed by stirring with a magnetic stirrer for 5 minutes. The particle diameter of each of the aqueous emulsions obtained was measured with a dynamic light scattering particle diameter analyzer FPAR-1000 (manufactured by Otsuka Electronics Co., Ltd.) at 25° C. The value of an average particle diameter was shown by a median diameter.

(Stability of Powder Over Time)

Each of the powders A-2 to K-2 obtained above was placed in a glass bottle with a cap, and the glass bottle was stored in a thermostatic bath maintained at 50° C. for four weeks.

Average Particle Diameter

The average particle diameters of the particles in the solutions obtained by redissolving in water each of powders A-2 to K-2 were measured at 25° C. according to the particle diameter measurement method described above.

The results are shown in Tables 3 and 4.

The results indicate that the powder samples according to the invention showed a high yield at spray drying, and the liquids obtained by redissolving the powder samples according to the invention had small average particle diameters, and the liquids were transparent.

Therefore, according to the invention, a powder composition is provided which enables protection of fine oil droplets during dry storage and provides transparency even after redissolution.

TABLE 3

| | | Encapsulating agent | Encapsulating agent/ oil component ratio | Lecithin | Polyglycerin fatty acid ester | Sucrose fatty acid ester |
|---|---|---|---|---|---|---|
| A-2 | Invention | Raffinose | 5.2 | Included | Included | Included |
| B-2 | Invention | Stachyose | 5.2 | Included | Included | Included |
| C-2 | Comparative Example | Maltotriose | 5.2 | Included | Included | Included |

TABLE 3-continued

|   | | Encapsulating agent | Encapsulating agent/ oil component ratio | Lecithin | Polyglycerin fatty acid ester | Sucrose fatty acid ester |
|---|---|---|---|---|---|---|
| D-2 | Comparative Example | Kestose | 5.2 | Included | Included | Included |
| E-2 | Comparative Example | Palatinose | 5.2 | Included | Included | Included |
| F-2 | Comparative Example | Lactose | 5.2 | Included | Included | Included |
| G-2 | Comparative Example | Gum arabic | 5.2 | Included | Included | Included |
| H-2 | Comparative Example | Modified starch | 5.2 | Included | Included | Included |
| I-2 | Invention | Raffinose | 2.6 | Included | Included | Included |
| J-2 | Invention | Raffinose | 5.2 | Included | Included | Not Included |
| K-2 | Invention | Raffinose | 5.2 | Included | Not Included | Included |

TABLE 4

|   | | Spray Dry Yield (%) | Average particle diameter at redispersion (nm) |
|---|---|---|---|
| A-2 | Invention | 85 | 103 |
| B-2 | Invention | 89 | 106 |
| C-2 | Comparative Example | 75 | 165 |
| D-2 | Comparative Example | 73 | 147 |
| E-2 | Comparative Example | 45 | 189 |
| F-2 | Comparative Example | 56 | 175 |
| G-2 | Comparative Example | 77 | 295 |
| H-2 | Comparative Example | 65 | 320 |
| I-2 | Invention | 91 | 120 |
| J-2 | Invention | 80 | 99 |
| K-2 | Invention | 86 | 115 |

All publications, patent applications, and technical standards mentioned in this specification are herein incorporated by reference to the same extent as if such individual publication, patent application, or technical standard was specifically and individually indicated to be incorporated by reference. It will be obvious to those having skill in the art that many changes may be made in the above-described details of the preferred embodiments of the present invention. The scope of the invention, therefore, should be determined by the following claims.

The invention claimed is:

1. A powder composition comprising a functional oil material, wherein the powder composition is obtained by drying an emulsion composition comprising at least one functional oil component, at least one emulsifier, and at least one water-soluble encapsulating agent,
wherein the functional oil component is a carotenoid,
wherein the water-soluble encapsulating agent encapsulates an oil phase containing the functional oil component and is selected from a polymer having from 2 to 23 fructose units or an oligomer having from 2 to 23 fructose units, and
wherein when the powder composition is added to an aqueous solution in an amount of 1% by mass of the powder composition with respect to the total amount of the aqueous solution, emulsion particles are formed having an average particle diameter from 10 to 500 nm.

2. The powder composition according to claim 1, wherein the at least one emulsifier is selected from sucrose fatty acid esters, polyglycerin fatty acid esters and phospholipids.

3. The powder composition according to claim 1, wherein the functional oil component is a carotenoid colorant.

4. The powder composition according to claim 3, wherein the carotenoid colorant is a natural extract containing astaxanthin and/or its ester.

5. The powder composition according to claim 4, wherein the carotenoid colorant is a *Haematococcus alga* colorant extract.

6. A food composition comprising the powder composition according to claim 1.

7. A cosmetic composition comprising the powder composition according to claim 1.

8. A pharmaceutical composition comprising the powder composition according to claim 1.

9. The powder composition according to claim 1, wherein the content of the water-soluble encapsulating agent is from 1 to 20 times the mass of the oil phase containing the functional oil component.

10. The powder composition according to claim 1, wherein the content of the water-soluble encapsulating agent is from 30 to 95% by mass based on the total mass of the powder composition.

11. The powder composition according to claim 4, wherein the total amount of the emulsifier is a range of from 10 to 1,000% by mass based on the oil phase containing the functional oil component.

12. A method for producing a powder composition containing a functional oil component, the method comprising:
emulsifying at least one functional oil component in an aqueous medium in the presence of at least one emulsifier selected from sucrose fatty acid esters, polyglycerin fatty acid esters and phospholipids to obtain an emulsion composition;
adding to the aqueous medium and/or the emulsion composition at least one water-soluble encapsulating agent,
wherein the functional oil component is a carotenoid,
wherein the water-soluble encapsulating agent encapsulates an oil phase containing the functional oil component and is selected from a polymer having from 2 to 23 fructose units or an oligomer having from 2 to 23 fructose units, and
drying the emulsion composition containing the water-soluble encapsulating agent;
wherein when the powder composition is added to an aqueous solution in an amount of 1% by mass of the powder composition with respect to the total amount of the aqueous solution, emulsion particles are formed having an average particle diameter from 10 to 500 nm.

* * * * *